United States Patent
Newton

(10) Patent No.: US 11,446,174 B2
(45) Date of Patent: Sep. 20, 2022

(54) MICRO-CLIMATE-MANAGED SKIN CARE, INCLUDING WOUND CARE

(71) Applicant: PureWick Corporation, El Cajon, CA (US)

(72) Inventor: Camille Rose Newton, Bonsall, CA (US)

(73) Assignee: PureWick Corporation, El Cajon, CA (US)

( * ) Notice: Subject to any disclaimer, the term of this patent is extended or adjusted under 35 U.S.C. 154(b) by 1039 days.

(21) Appl. No.: 15/384,196

(22) Filed: Dec. 19, 2016

(65) Prior Publication Data

US 2018/0168853 A1    Jun. 21, 2018

(51) Int. Cl.
*A61F 7/00* (2006.01)
*A61F 13/00* (2006.01)
(Continued)

(52) U.S. Cl.
CPC .............. *A61F 7/00* (2013.01); *A61F 7/0053* (2013.01); *A61F 13/00068* (2013.01);
(Continued)

(58) Field of Classification Search
CPC .. A61F 7/00; A61F 7/0053; A61F 2007/0052; A61F 2007/0058;
(Continued)

(56) References Cited

U.S. PATENT DOCUMENTS 1,979,899 A * 11/1934 O'Brien ................. A61F 13/505
604/393
3,042,041 A * 7/1962 Jascalevich ........... A61M 27/00
604/277
(Continued)

FOREIGN PATENT DOCUMENTS

EP        2567682 A1    3/2013
JP    H09503923 A       4/1997
(Continued)

OTHER PUBLICATIONS

Definition of Sump (Year: 2020).*
(Continued)

*Primary Examiner* — Nicholas J. Weiss
*Assistant Examiner* — Gabriella E Burnette
(74) *Attorney, Agent, or Firm* — Dorsey & Whitney LLP

(57) ABSTRACT

A skin care device includes a receptacle that includes an outlet port and defines a chamber that extends from the outlet port to a sump, which is defined by an impermeable portion of the receptacle, and is disposed for receiving one end of a tube inserted through the outlet port. Wicking material is received over a permeable portion of the receptacle for location over a particular region of the skin. When a vacuum is applied at the sump, the particular region is cooled by evaporative cooling when the particular region is moist. The device includes at least one vent that is so disposed as to promote air flow and to prevent a vacuum from occurring at a portion of the skin adjacent where the wicking material is located while the vacuum is applied. The device can be used for wound care and to dispose wicking material within a skin fold.

13 Claims, 2 Drawing Sheets

(51) Int. Cl.
*A61M 1/00* (2006.01)
*A61F 7/02* (2006.01)

(52) U.S. Cl.
CPC ..... *A61M 1/964* (2021.05); *A61F 2007/0021* (2013.01); *A61F 2007/0037* (2013.01); *A61F 2007/0052* (2013.01); *A61F 2007/0058* (2013.01); *A61F 2007/0239* (2013.01); *A61M 1/85* (2021.05); *A61M 2205/3606* (2013.01); *A61M 2210/04* (2013.01); *A61M 2210/08* (2013.01)

(58) Field of Classification Search
CPC ...... A61F 2007/0239; A61F 2007/0037; A61F 2007/0021; A61F 13/00068; A61F 2007/0029; A61F 2007/0036; A61F 2007/0038; A61F 2007/005; A61F 2007/0056; A61F 2007/0063; A61F 2007/0001; A61F 7/10; A61M 1/0092; A61M 1/0084; A61M 2210/04; A61M 2210/08; A61M 2205/3606; F24F 3/044; F24F 3/14; F24F 5/0096; A47C 21/044
See application file for complete search history.

(56) References Cited

U.S. PATENT DOCUMENTS

| | | | |
|---|---|---|---|
| 4,415,680 A | | 11/1983 | Ushirokawa et al. |
| 5,678,564 A | * | 10/1997 | Lawrence ............... A61F 5/455 600/574 |
| 7,144,390 B1 | * | 12/2006 | Hannigan ................. A61F 7/10 604/313 |
| 7,975,331 B2 | * | 7/2011 | Flocard ............. A61G 7/05784 5/423 |
| 9,222,685 B2 | * | 12/2015 | Lachenbruch ........ F24F 5/0096 |
| 2001/0029956 A1 | * | 10/2001 | Argenta .............. A61F 13/0246 128/897 |
| 2005/0197639 A1 | * | 9/2005 | Mombrinie ............... A47L 9/02 604/317 |
| 2006/0079852 A1 | | 4/2006 | Bubb et al. |
| 2009/0254053 A1 | * | 10/2009 | Svensby ............. A61F 13/0203 604/290 |
| 2010/0312159 A1 | | 12/2010 | Aali et al. |
| 2012/0143665 A1 | | 6/2012 | Swain et al. |
| 2013/0245527 A1 | * | 9/2013 | Croizat ............... A61F 13/0216 602/43 |
| 2014/0123981 A1 | * | 5/2014 | Willard ..................... C08J 9/00 128/205.25 |

FOREIGN PATENT DOCUMENTS

| | | |
|---|---|---|
| JP | 2003510106 A | 3/2003 |
| JP | 2003532504 A | 11/2003 |
| JP | 2009509695 A | 3/2009 |
| JP | 2009220829 A | 10/2009 |
| JP | 2009542408 A | 12/2009 |
| JP | 2011530344 A | 12/2011 |
| JP | 2014527418 A | 10/2014 |
| JP | 2016511047 A | 4/2016 |
| KR | 20080066764 A | 7/2008 |
| KR | 20090027727 A | 3/2009 |
| WO | 0185248 A1 | 11/2001 |
| WO | 2008008032 A1 | 1/2008 |
| WO | 2012143665 A1 | 10/2012 |

OTHER PUBLICATIONS

SAATICare product information (Year: 2020).*
International Search Report and Written Opinion for International Application No. PCT/US2017/066306 dated Feb. 22, 2018.

* cited by examiner

US 11,446,174 B2

MICRO-CLIMATE-MANAGED SKIN CARE, INCLUDING WOUND CARE

BACKGROUND OF THE INVENTION

The present invention generally pertains to skin care and is particularly directed to a device and method for caring for the skin of a person by micro-climate management of the skin, including wound care.

U.S. Pat. No. 9,222,685 to Lachenbruch teaches that care of a particular region of the skin of a person is enhanced by micro-climate management of the particular region of the skin, such as by causing air to flow over the particular region of the skin in order to cool the particular region of the skin by evaporation. Air movement enables evaporative cooling.

SUMMARY OF THE INVENTION

The invention provides a device for caring for a particular region of the skin of a person by managing the micro-climate of the particular region of the skin, comprising: a receptacle including an outlet port and defining a chamber that extends from the outlet port to a sump that is defined by an impermeable portion of the receptacle and is disposed for receiving one end of a tube inserted through the outlet port, with the chamber being shaped to receive fluid drawn into the chamber through a permeable portion of the receptacle, wherein fluid can be drawn into the chamber by a vacuum applied at the sump; wherein the receptacle is configured to receive a wicking material over at least some of the permeable portion of the receptacle and is also configured and dimensioned for locating at least some of the wicking material over at least a portion of a particular region of the skin, so that upon said location of the said wicking material, when a vacuum is applied at the sump, said at least a portion of the particular region of the skin is cooled by evaporative cooling when the particular region is moist.

The invention also provides a method of caring for a particular region of the skin of a person by managing the micro-climate of the particular region of the skin, comprising the steps of:

(a) applying to at least a portion of a particular region of the skin, a device comprising a receptacle including an outlet port and defining a chamber that extends from the outlet port to a sump that is defined by an impermeable portion of the receptacle and is disposed for receiving one end of a tube inserted through the outlet port, with the chamber being shaped to receive fluid drawn into the chamber through a permeable portion of the receptacle; wherein fluid can be drawn into the chamber by a vacuum applied at the sump; wherein a wicking material is received over at least some of the permeable portion of the receptacle, and the receptacle is configured and dimensioned for locating at least some of the wicking material over at least a portion of the particular region of the skin, so that upon said location of the wicking material, when a vacuum is applied at the sump, said at least a portion of the particular region of the skin is cooled by evaporation and wherein an impermeable layer covers at least a portion of the device that is not configured for locating the wicking material over said at least a portion of the particular region of the skin; and (b) applying a vacuum at the sump to cause air to be drawn from at least a portion of the particular region of the skin to thereby cool said at least a portion of the particular region by evaporative cooling when the particular region is moist.

A device according to the invention can be used for treating a wound in a particular region of the skin.

The invention further provides a method of caring for a wound in a particular region of the skin of a person by managing the micro-climate of the particular region of the skin, comprising the steps of:

(a) applying to a wound in a particular region of the skin, a device comprising a receptacle including an outlet port and defining a chamber that extends from the outlet port to a sump that is defined by an impermeable portion of the receptacle and is disposed for receiving one end of a tube inserted through the outlet port, with the chamber being shaped to receive fluid drawn into the chamber through a permeable portion of the receptacle; wherein fluid can be drawn into the chamber by a vacuum applied at the sump; wherein a wicking material is received over at least some of the permeable portion of the receptacle, and the receptacle is configured and dimensioned for locating at least some of the wicking material over the wound in the particular region of the skin, so that upon said location of the wicking material, when a vacuum is applied at the sump, the wound in the particular region of the skin is cooled by evaporative cooling when the particular region is moist; and wherein an impermeable layer covers at least a portion of the device that is not configured for locating the wicking material over said at least a portion of the particular region of the skin; and (b) treating the wound in the particular region of the skin by the steps of:

(c) irrigating the wound by inserting liquid into the chamber through an irrigation port in the receptacle and thence through the wicking material to the wound in the particular region of the skin; and (d) applying a vacuum at the sump to cause the wound to be cooled by evaporative cooling when the wound is moist and to cause the wound to be debrided.

In addition to cooling at least a portion of the particular region of the skin by evaporative cooling, the invention prevents a vacuum from occurring at a portion of the skin of said person adjacent where said wicking material is so located while said vacuum is being applied, by applying to said at least a portion of the particular region of the skin during step (a) a said device in which at least one vent is disposed in a portion of the impermeable layer and/or a portion of the receptacle that is so disposed as to not contact the skin of the person while the wicking material is located over at least said portion of said particular region of the skin.

Additional features of the invention are described with reference to the detailed description.

These figures are not drawn to scale or to illustrate the shapes of the various components of the exemplary embodiments, but are drawn merely for the purpose of showing the relative placement of the various components.

DETAILED DESCRIPTION

Figure 1:
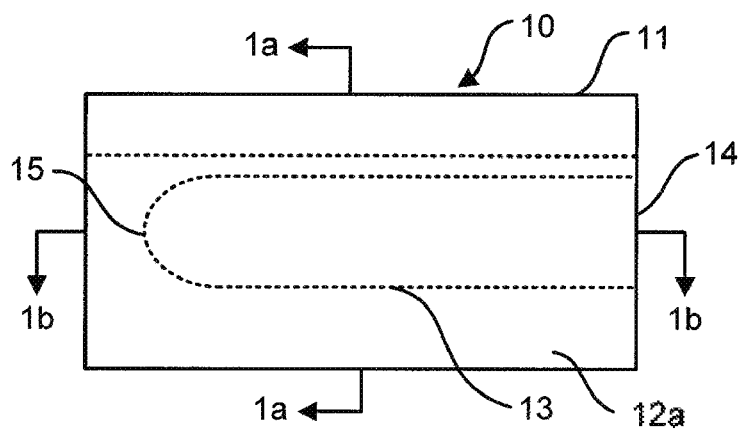
FIG. 1 is a schematic view of an exemplary embodiment of a skin care device according to the invention, with an interior chamber being shown by dashed lines.
Figure 1A:
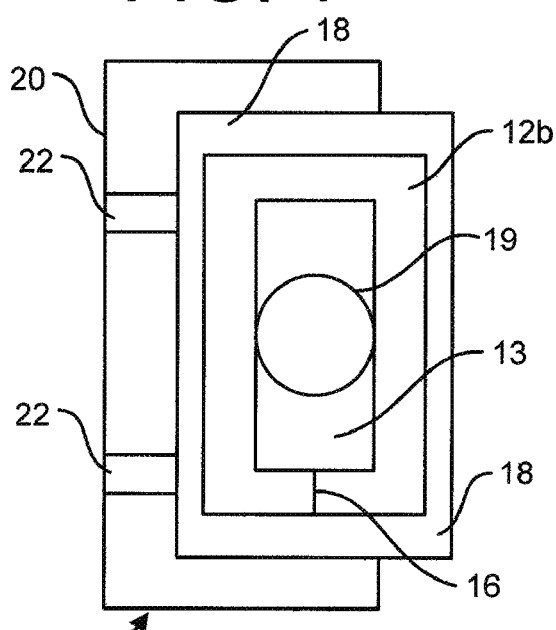
FIG. 1A is a schematic sectional end view of the receptacle shown in FIG. 1, taken along line 1a-1a in FIG. 1, and further showing a tube received in the interior chamber through an outlet port and wicking material covering a portion of a receptacle.
Figure 1B:
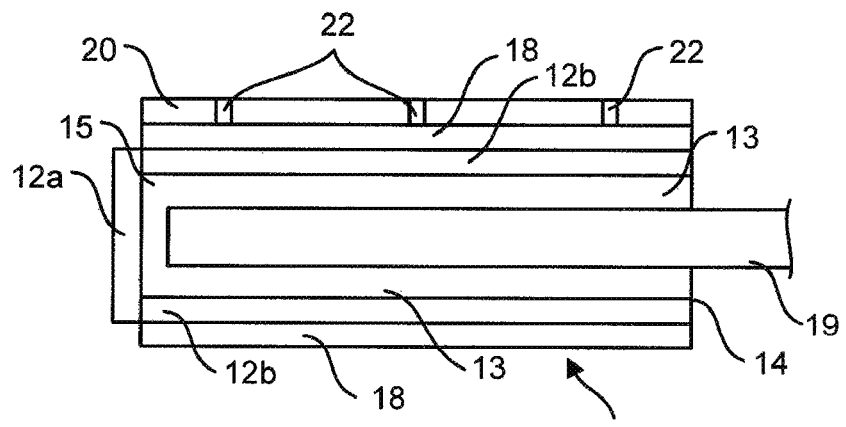
FIG. 1B is a schematic sectional side view of the receptacle shown in FIG. 1, taken along line 1b-1b in FIG. 1, and further showing a tube received in the interior chamber through the outlet port and wicking material covering a portion of the receptacle.

Referring to FIGS. 1, 1A and 1B, one exemplary embodiment of a skin care device 10 according to the invention includes a receptacle 11. The receptacle includes an outlet port 14 and defines a chamber 13 that extends from the outlet port 14 to a sump 15. The sump 15 is defined by an impermeable portion 12a of the receptacle 11 and is disposed for receiving one end of a tube 19 inserted through the outlet port 14. Preferably the tube 19 is so received in the chamber 13 that the open end of the tube 19 extends into the sump 15 and enables a sucking action in the sump 15, like the suction action provided when one sucks on a straw.

The chamber 13 is shaped to receive fluid drawn into the chamber 13 through a permeable portion 12b of the receptacle 11. The permeable portion 12b comprises a first and second portion which are spaced apart from each other. Fluid can be drawn into the chamber 13 by a vacuum applied at the sump 15 by the tube 19. The chamber 13 can be any shape and typically is more flattened than circular.

The receptacle 11 is configured to receive a wicking material 18 over at least some of the permeable portion 12b of the receptacle 11, and is also configured and dimensioned for locating at least some of the wicking material 18 over at least a portion of a particular region of the skin, so that upon such location of the wicking material 18, when a vacuum is applied at the sump 15, the particular region of the skin is cooled by evaporative cooling when the particular region is moist.

The wicking material 18 is selected from such exemplary materials as a fabric and a non-woven material (such as gauze) that defines a very large number of potential paths for air and liquid to pass without inhibiting the micro-climate management.

In this exemplary embodiment of the skin care device 10, the permeable portion 12b of the receptacle 11 includes a web of spun plastic material having a very large number of small openings. In one version of this exemplary embodiment, the permeable web of spun plastic material is a sheet that is configured to define the cross-section of the chamber 13 by flexing and folding over the sheet so that opposing sides of the sheet are held closely together, or meet (as shown at 16). The opposing sides of the permeable web can be held together by adhesive bands, or by other means, such as glue, or by compression that is created when some article, such as wicking material 18 (FIG. 1B), is wrapped around the sheet. In some other embodiments, the opposing edges of the permeable web do not meet.

Figure 3:
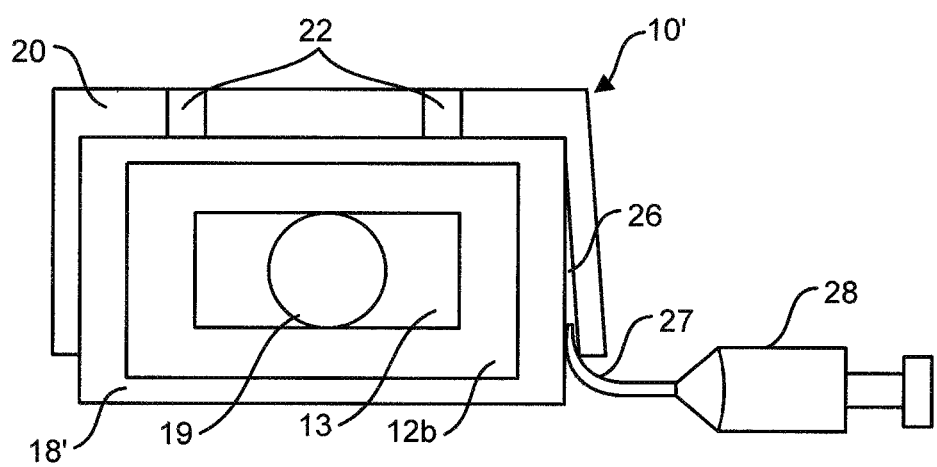
FIG. 3 is a schematic partial sectional end view of another exemplary embodiment of a device according to the invention, further including an irrigation port and showing a syringe that can be used in combination with the irrigation port for irrigating a particular region of the skin.

Although the chamber 13 is illustrated as having a rectangular cross-section in FIGS. 1A and 3, the permeable portion 12b of the receptacle 11 preferably is configured to define a chamber 13 having some other cross-sectional shape, such as whatever cross-sectional shape is adequate to receive a tube 19, such as the chamber between two opposing receptacles of a folded-over sheet of flexible spun plastic material.

In one exemplary embodiment, in which the wicking material 18 is received to cover at least some of the permeable portion 12b of the receptacle 11, the skin care device 10 also includes an impermeable layer 20. The impermeable layer 20 is not disposed on the side of the wicking material 18 that is disposed for placement against at least a portion of a particular exposed region of the skin. The impermeable layer 20 covers at least a portion of the device 10 that is not configured for locating the wicking material 18 over a portion of the particular region of the skin. The impermeable layer 20 helps to decrease loss of vacuum and to prevent liquids from leaking out of the skin care device 10 and soaking the patient and/or the user's clothes, while still permitting air flow through the uncovered portion of the wicking material 18.

FIG. 1A shows the wicking material 18 as being received by the permeable portion 12b of the receptacle 11 fully around the cross-sectional periphery of the permeable portion 12b of the receptacle 11. In alternative embodiments in which the receptacle 11 is not configured for receiving the wicking material 18 fully around the cross-sectional periphery of the permeable portion 12b of the receptacle 11, the permeable portion 12b of the receptacle 11 is also not necessarily disposed around the cross-sectional periphery of the chamber 13.

In some such alternative embodiments, the impermeable portion 12a of the receptacle 11 merges with the impermeable layer 20, and the permeable portion 12b of the receptacle 11 is not necessarily disposed beneath the impermeable layer 20 (unlike such as shown in FIG. 1B), whereby the impermeable layer 20 defines a portion of the longitudinal extension of the chamber 13.

An impermeable layer 20 is not necessary when caring for such regions of the skin where skin overlies skin, such as within a skin fold, under the person's breasts, under the person's abdominal pannus, within the person's axillae, or in a portion of the person's groin area, because body folds of skin in these regions prevent loss of vacuum; whereby the wicking material is adequate to provide evaporative cooling when the vacuum is applied.

At least one vent is disposed in a portion of the impermeable layer 20 and/or a portion of the receptacle 11 that is so disposed as to not contact the skin of the person while the wicking material 18 is located over said at least a portion of the particular region of the skin as to promote the drawing of air from at least such portion of the particular region of the skin and to prevent a vacuum from occurring at a portion of the skin where the wicking material 18 is so located while a vacuum is applied.

In the exemplary embodiment described herein with reference to FIGS. 1, 1A and 1B, at least one vent is provided by holes 22 in the impermeable layer 20.

In some alternative embodiments, at least one vent can be provided by the impermeable layer 20 not covering the wicking material 18 at the location of the vent, such as at the end of the receptacle 11 that includes the outlet port 14, since the wicking material 18 is naturally vented. A vent cannot be located in the vicinity of the sump 15. Otherwise, the location of the vent is a matter of design choice.

In some alternative embodiments, at least one vent can be disposed in an impermeable portion of the receptacle 11 that is not configured to receive the wicking material 18 or to contact the skin while the skin care device 10 is being used to care for the skin.

In one exemplary embodiment, each vent is provided by a hole 22 having a diameter of about two millimeters. The size and shape of the holes 22 may be different in other embodiments. In some embodiments, the at least one vent may be other than circular, such as a slit. The at least one vent need be of such shape and size as to prevent a vacuum from occurring at a portion of the skin of a person or an animal that is adjacent where the wicking material 18 is placed while air is flowing through the wicking material 18.

Figure 2:
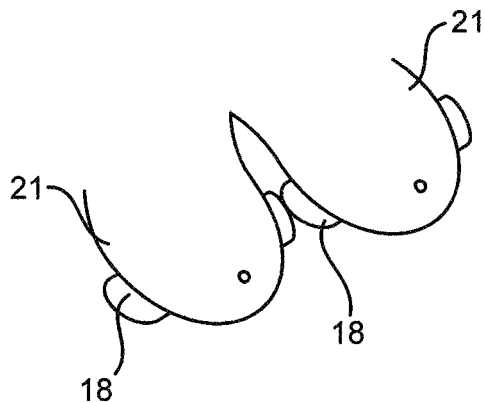
FIG. 2 illustrates an exemplary use of the wicking material of a device according to the invention to care for a region where skin overlies skin.

The vents must be exposed to the air when using the device 10 to care for those regions of the skin where skin overlies skin where an impermeable layer is unnecessary, as described above. For example, when the wicking material 18 is disposed under a breast 21, as shown in FIG. 2, a vent is provided by exposure of the wicking material 18 on at least one side of the breast 21.

Referring to FIG. 3, in another exemplary embodiment, the skin care device 10' also includes an irrigation port 26. Although the location of the irrigation port 26 is a matter of design choice, in one embodiment, the irrigation port 26 is disposed between the wicking material 18 and impermeable layer 20.

A tube 27 extending from a syringe 28 is inserted into the irrigation port 26 and a wound in the particular region of the skin is irrigated by using the syringe to insert liquid into the chamber 13 through the irrigation port 26 and thence through the wicking material 18 to the particular region of the skin. When the particular region of the skin includes a wound, the wound can be mechanically debrided by applying a vacuum at the sump to cause dead tissue and fluid to be wicked from the wound by the wicking material 18' and to be drawn into the sump though the permeable portion 12b of the receptacle and to be carried from the sump through the received tube 19.

Such irrigation can cleanse a wound in the particular region of the skin at which the wicking material 18 is applied. Such irrigation can also provide medications and beneficial enzymes to such particular region and also provide liquid to enable evaporative cooling and to moisturize the skin.

Figure 4:
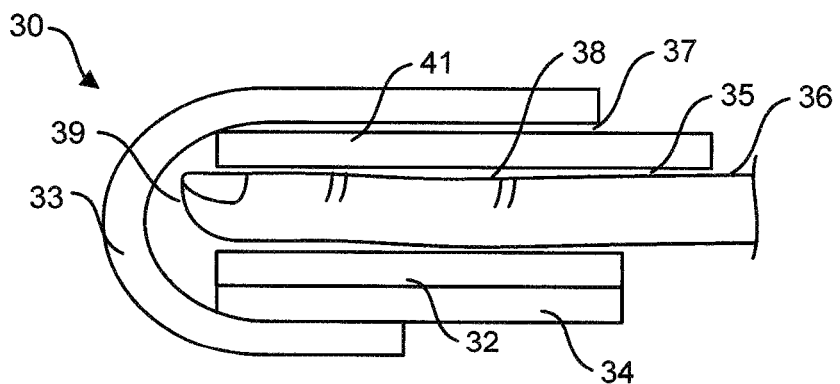
FIG. 4 is a schematic partial-sectional side view of still another exemplary embodiment of a device according to the invention, further including a finger pocket.

Referring to FIG. 4, another exemplary embodiment of a skin care device 30, according to the invention includes a receptacle, The device 30 includes a permeable portion 32 and an impermeable portion 33, wicking material 34 covering a portion of the permeable portion 32 and a finger pocket 35 disposed adjacent a portion of the wicking material 34 that is disposed for location over at least a portion of the particular region of the skin The finger pocket 35 is configured for being fitted over a finger 36. The device 30 also includes an outlet port 37 and defines a chamber 38 that extends from the outlet port 37 to a sump 39. The sump 39 is defined by portion of the impermeable portion 33 of the receptacle, and is disposed for receiving one end of a tube 41 inserted through the outlet port 37. Preferably the tube 41 is so received in the chamber 38 that the open end of the tube 41 extends into the sump 39 and enables a sucking action in the sump 39.

A vacuum is applied to the sump while the finger pocket 35 is being used.

Also, the particular region of the skin can be irrigated by use of a syringe (not shown) inserted into an irrigation port (such as shown at 26 in FIG. 3, while the finger pocket 35 is being used.

A surgeon or a nurse can insert a finger 36 into the finger pocket 35; and use the inserted finger 36 to position the device 30 while irrigating a particular region of the skin with a syringe to thereby keep the particular region of the skin clean and thus enable better visibility of the particular region of the skin during surgery or while irrigating a wound.

When a finger 36 is inserted in the finger pocket 35 during surgery, operating team personnel can use the finger pocket 32 to position the wicking material 32 over a hole in a perforated organ in order to remove blood and other fluid from the hole in the perforated organ.

The device 30 is used to cool the portion of the particular region of the skin to which the wicking material 34 is applied by evaporative cooling when the particular region is moist by applying a vacuum at the sump 39.

The device 30 also can be used to care for those regions of the skin where skin overlies skin, as described above.

Examples of use of various embodiment of the invention include caring for skin that is impaired by injury or disease, and to remove undesired moisture from wounds or other particular regions of the skin, such as between folds of skin or under breasts. For such moisture removal uses, the skin care device preferably does not include an impermeable barrier that would inhibit the flow of moisture through the chamber.

The benefits specifically stated herein do not necessarily apply to every conceivable embodiment of the invention. Further, such stated benefits of the present invention are only examples and should not be construed as the only benefits of the invention.

While the above description contains many specificities, these specificities are not to be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A device for caring for a particular region of the skin of a person by managing the micro-climate of the particular region of the skin, comprising:
 a receptacle including:
  an outlet port;
  a permeable portion having a first permeable region and a second permeable region spaced from each other to at least partially define a space therebetween, the first permeable region and the second permeable region at least partially defining a chamber in the space between the first permeable region and the second permeable region that extends inward from the outlet port;
  an impermeable portion; and
  a sump disposed for receiving one end of a tube inserted through the outlet port and the space between the first permeable region and the second permeable region, with the chamber being shaped in the space between the first permeable region and the second permeable region to receive fluid drawn into the chamber through at least the first permeable region of the permeable portion of the receptacle, wherein fluid can be drawn into the chamber by a vacuum applied at the sump, wherein the receptacle is configured to receive a wicking material over at least the first permeable region of the permeable portion of the receptacle and is also configured and dimensioned for locating at least some of the wicking material on the first permeable region of the permeable portion over at least a portion of a particular region of the skin, so that upon said location of the said wicking material, when a vacuum is applied at the sump, said at least a portion of the particular region of the skin is cooled by evaporative cooling when the particular region is moist; and an impermeable layer covering at least a portion of the receptacle such that the chamber is positioned between at least a portion of the impermeable layer and the first permeable region of the permeable portion; and at least one vent positioned to promote drawing of air into the chamber through the second permeable region of the permeable portion, the at least one vent extending through at least the portion of the impermeable layer or being positioned proximate to the outlet port between the outlet port and the impermeable layer.

2. The device according to claim 1, further comprising said wicking material that is so received by the receptacle such that the first permeable region is at least partially directly between the wicking material and the chamber, the wicking material including gauze.

3. The device according to claim 2, further comprising a finger pocket that is disposed adjacent a portion of the wicking material that is disposed for location over at least a portion of the particular region of the skin, with the pocket being configured for being fitted over a finger.

4. The device according to claim 2, wherein the receptacle includes an irrigation port into which liquid can be inserted into the chamber and thence through the wicking material to said particular region of the skin.

5. The device according to claim 1, wherein the receptacle further includes an irrigation port into which liquid can be inserted into the chamber.

6. The device according to claim 1, wherein the permeable portion of the receptacle comprises a spun plastic material having a large number of small openings.

7. A method of caring for a particular region of the skin of a person by managing the micro-climate of the particular region of the skin, comprising the steps of:

(a) applying to at least a portion of a particular region of the skin, at least a portion of a receptacle of a device, the receptacle including (1) an outlet port, (2) a permeable portion having a first permeable region and a second permeable region spaced from each other to at least partially define a space therebetween, the first permeable region and the second permeable region at least partially defining a chamber in the space between the first permeable region and the second permeable region that extends inward from the outlet port, (3) an impermeable portion, and (4) a sump disposed for receiving one end of a tube inserted through the outlet port and the space between the first permeable region and the second permeable region, with the chamber being shaped in the space between the first permeable region and the second permeable region to receive fluid drawn into the chamber through at least the first permeable region of the permeable portion of the receptacle; wherein fluid can be drawn into the chamber by a vacuum applied at the sump; wherein a wicking material is received over at least of the first permeable region of the permeable portion of the receptacle, and the receptacle is configured and dimensioned for locating at least some of the wicking material over at least a portion of the particular region of the skin, so that upon said location of the wicking material, when a vacuum is applied at the sump, at least a portion of the particular region of the skin is cooled by evaporative cooling when the particular region is moist; and wherein an impermeable layer covers at least a portion of the receptacle such that the chamber is positioned between at least a portion of the impermeable layer and the at least some of the permeable portion; and (b) causing at least a portion of the particular region of the skin to be cooled by evaporative cooling when the particular region is moist by applying a vacuum at the sump, wherein the device includes at least one vent to promote drawing of air into the chamber through permeable portion when the vacuum is applied, the at least one vent extending through at least the portion of the impermeable layer or being positioned proximate to the outlet port between the outlet port and the impermeable layer.

8. The method according to claim 7, wherein:

step (a) comprises the step of (i) applying said device that includes an irrigation port into which liquid can be inserted into the chamber; and the method further comprises the step of (d) irrigating said particular region of the skin by inserting liquid into the chamber through the irrigation port and thence through the wicking material to said particular region of the skin.

9. A method of caring for a particular region of the skin of a person by managing the micro-climate of the particular region of the skin, comprising the steps of:

(a) applying to at least a portion of a particular region of the skin, a portion of a receptacle of a device, the receptacle including (1) an outlet port, (2) a permeable portion having a first permeable region and a second permeable region spaced from each other to at least partially define a space therebetween, the first permeable region and the second permeable region at least partially defining a chamber in the space between the first permeable region and the second permeable region that extends inward from the outlet port, (3) an impermeable portion, and (4) a sump disposed for receiving one end of a tube inserted through the outlet port and the space between the first permeable region and the second permeable region, with the chamber being shaped in the space between the first permeable region and the second permeable region to receive fluid drawn into the chamber through at least the first permeable region of the permeable portion of the receptacle; wherein fluid can be drawn into the chamber by a vacuum applied at the sump; wherein a wicking material is received over the first permeable region of the permeable portion of the receptacle, and the receptacle is configured and dimensioned for locating at least some of the wicking material on the first permeable region of the permeable portion over at least a portion of the particular region of the skin, so that upon said location of the wicking material, when the vacuum is applied at the sump, at least a portion of the particular region of the skin is cooled by evaporative cooling when the particular region is moist; and (b) causing at least a portion of the particular region of the skin to be cooled by evaporative cooling when the particular region is moist by applying the vacuum at the sump, wherein an impermeable layer covers a portion of the receptacle such that the chamber is positioned between at least a portion of the impermeable layer and the at least some of the permeable portion, the device including at least one vent to promote drawing of air into the chamber through permeable portion when the vacuum is applied, the at least one vent extending through at least the portion of the impermeable layer or being positioned proximate to the outlet port between the outlet port and the impermeable layer;

wherein step (a) comprising the step of:
(i) so applying said device that at least some of the wicking material is disposed within a skin fold, under the person's breasts, under the person's abdominal pannus, within the person's axillae, or over a portion of the person's groin area, wherein upon such application at least part of the wicking material and/or the permeable portion of the receptacle is exposed to air to in order to promote drawing of air from at least said portion of the particular region of the skin and to prevent a vacuum from occurring at a portion of the skin of said person adjacent where said wicking material is so located while said vacuum is applied.

10. A method of caring for a wound in a particular region of the skin of a person by managing the micro-climate of the particular region of the skin, comprising the steps of:
(a) applying to a wound in a particular region of the skin, a portion of a receptacle of a device, the receptacle including (1) an outlet, (2) a permeable portion having a first permeable region and a second permeable region spaced from each other to at least partially define a space therebetween, the first permeable region and the second permeable region at least partially defining a chamber in the space between the first permeable region and the second permeable region that extends inward from the outlet port, (3) an impermeable portion, and (4) a sump disposed for receiving one end of a tube inserted through the outlet port and the space between the first permeable region and the second permeable region, with the chamber being shaped in the space between the first permeable region and the second permeable region to receive fluid drawn into the chamber through at least the first permeable region of the permeable portion of the receptacle; wherein fluid can be drawn into the chamber by a vacuum applied at the sump; wherein a wicking material is received over at least the first permeable region of the permeable portion of the receptacle, and the receptacle is configured and dimensioned for locating at least some of the wicking material on the first permeable region of the permeable portion over the wound in the particular region of the skin, so that upon said location of the wicking material, when a vacuum is applied at the sump, the wound in the particular region of the skin is cooled by evaporative cooling when the particular region is moist; and wherein an impermeable layer covers at least a portion of the receptacle such that the chamber is positioned between at least a portion of the impermeable layer and the at least some of the permeable portion; and
(b) treating the wound in the particular region of the skin by the steps of:
(i) irrigating the wound by inserting liquid into the chamber through an irrigation port in the receptacle and thence through the wicking material to the wound in the particular region of the skin; and
(ii) applying a vacuum at the sump to cause the wound to be cooled by evaporative cooling when the wound is moist and to cause the wound to be debrided, the impermeable layer including at least one vent in the device that promotes drawing of air into the chamber through the permeable portion when the vacuum is applied, that least one vent extending through at least the portion of the impermeable layer or being positioned proximate to the outlet port between the outlet port and the impermeable layer.

11. The method according to claim 10, further comprising the step of:
(c) preventing a vacuum from occurring at a portion of the skin of said person adjacent where said wicking material is so located while said vacuum is being applied, by applying to said at least a portion of the particular region of the skin during step (a) said device in which at least one vent is disposed in a portion of the impermeable layer and/or a portion of the receptacle that is so disposed as to not contact the skin of the person while the wicking material is located over at least said portion of said particular region of the skin.

12. The device according to claim 2, wherein the at least one vent is positioned to promote drawing of the air into the chamber through the wicking material and the permeable portion.

13. The device according to claim 12, wherein at least some of the wicking material is positioned between the permeable portion and the portion of the impermeable layer, and the at least one vent extends through at least the portion of impermeable layer to promote drawing of the air into the chamber through the wicking material and the permeable portion.

* * * * *